(12) United States Patent
Gergely et al.

(10) Patent No.: US 9,102,716 B2
(45) Date of Patent: Aug. 11, 2015

(54) PEPTIDE DERIVATIVES FOR BIOFUNCTIONALIZATION OF SILICON SUBSTRATES AND THEIR APPLICATIONS

(75) Inventors: Csilla Gergely, Montpellier (FR); Elias Estephan, Reims (FR); Marie-belle Saab, Reims (FR); Christian Larroque, Montferrier sur Lez (FR); Frédéric Cuisinier, Montpellier (FR)

(73) Assignees: Centre National de la Recherche Scientifique, Paris (FR); Universite Montpellier I, Montpellier (FR)

( * ) Notice: Subject to any disclaimer, the term of this patent is extended or adjusted under 35 U.S.C. 154(b) by 0 days.

(21) Appl. No.: 13/695,913

(22) PCT Filed: May 5, 2011

(86) PCT No.: PCT/IB2011/051999
§ 371 (c)(1),
(2), (4) Date: Jan. 9, 2013

(87) PCT Pub. No.: WO2011/138757
PCT Pub. Date: Nov. 10, 2011

(65) Prior Publication Data
US 2013/0131314 A1    May 23, 2013

(30) Foreign Application Priority Data
May 5, 2010  (EP) .................................... 10290242

(51) Int. Cl.
*C07K 17/14*  (2006.01)
*C07K 7/08*  (2006.01)
*G01N 33/543*  (2006.01)
*G01N 33/551*  (2006.01)

(52) U.S. Cl.
CPC . *C07K 17/14* (2013.01); *C07K 7/08* (2013.01); *G01N 33/54353* (2013.01); *G01N 33/551* (2013.01)

(58) Field of Classification Search
CPC .... C07K 17/14; C07K 7/08; G01N 33/54353; G01N 33/551
See application file for complete search history.

(56) References Cited

U.S. PATENT DOCUMENTS

2003/0224494 A1   12/2003 Nomoto et al.
2006/0275791 A1*  12/2006 Belcher et al. .................... 435/6
2009/0163405 A1    6/2009 Hardy et al.

FOREIGN PATENT DOCUMENTS

WO    03/026590    4/2003
WO    03/072599    9/2003

OTHER PUBLICATIONS

Matthew B. Dickerson, Identification and Design of Peptides for the Rapid, High-yield formation of Nanoparticulate TiO2 from Aqueous Solutions at Room temperture, Chem Mater., 2008, 20:1578-1584.*
Ken-Ichi Sano, Specificity and Biomineralization Activities of Ti-Binding Peptide-1 (TBP-1), Langmuir, 2005, 21, pp. 3090-3095.*
Luca De Stefano, Glutamine Binding Protein from *Escherichia* Cell Specifically binds a wheat gliadin peptide allowing the design of a New porous Silicon based optical biosenor, Journal of Proteome Research, 2006, 5(9):2083-2086.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Matthew B. Dickerson, Identification and Design of Peptides for the Rapid, High-yield formation of Nanoparticulate TiO2 from Aqueous Solutions at Room temperture, Chem Mater., 2008, Supplemental, pp. 1-12.*

* cited by examiner

*Primary Examiner* — James H Alstrum Acevedo
*Assistant Examiner* — Erinne Dabkowski
(74) *Attorney, Agent, or Firm* — Morgan, Lewis & Bockius LLP

(57) ABSTRACT

The present invention relates to the use of a peptide consisting of 5 to 30 amino acid residues comprising an amino acid sequence selected from LLADTTHHRPWT (SEQ ID NO: 1), SPGLSLVSHMQT (SEQ ID NO: 2), and the sequences presenting at least 80% identity with SEQ ID NO: 1 or SEQ ID NO: 2, for the functionalization of silicon substrate. The present invention also relates to the specific peptides as such, and to silicon substrates functionalized by the adsorption on their surface of such specific peptides. Finally, the present invention is also directed to a process for the preparation of such functionalized silicon substrates, and to articles comprising a silicon substrate according to the invention.

13 Claims, 11 Drawing Sheets a)

b)

Figure 1:
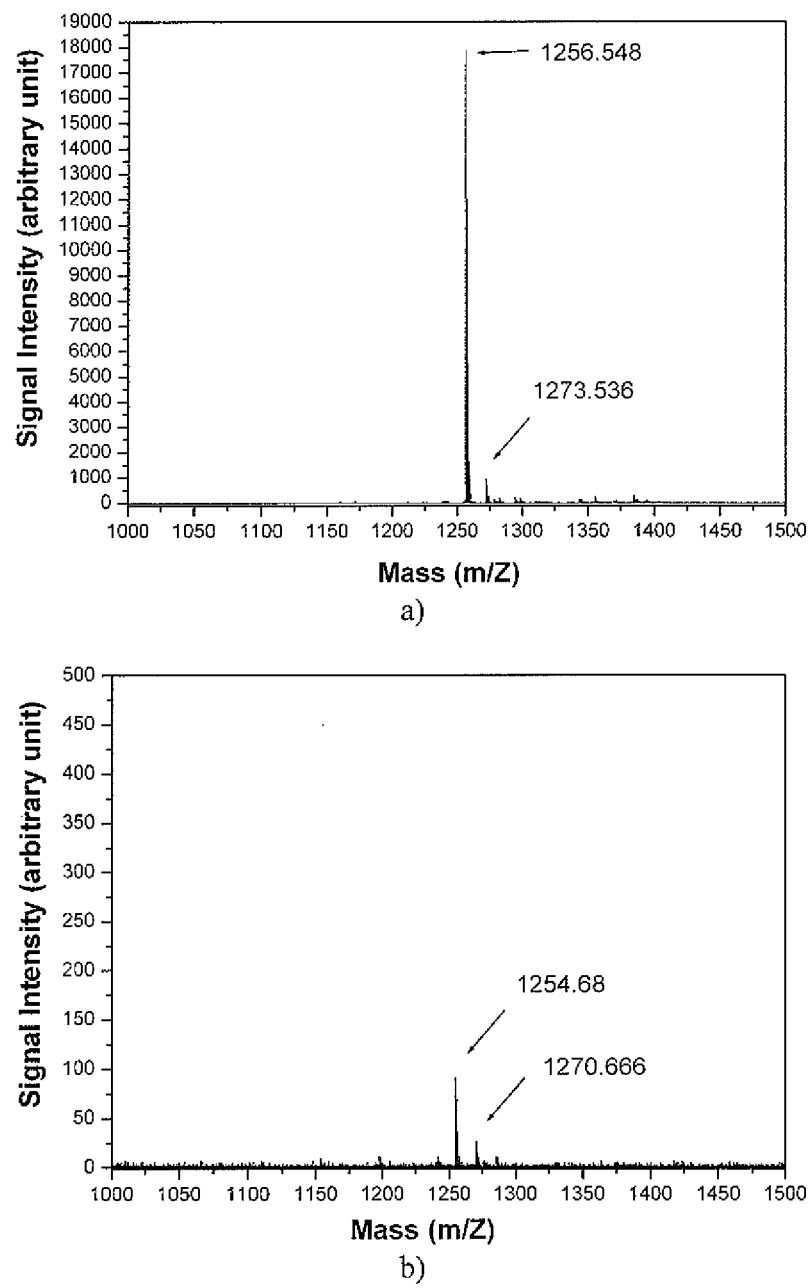

PEPTIDE DERIVATIVES FOR BIOFUNCTIONALIZATION OF SILICON SUBSTRATES AND THEIR APPLICATIONS

SEQUENCE LISTING SUBMISSION VIA EFS-WEB

A computer readable text file, entitled "045636-5212_SequenceListing.txt," created on or about Jan. 7, 2013, with a file size of about 4 kb contains the sequence listing for this application and is hereby incorporated by reference in its entirety.

The invention relates to the use of specific peptides for the functionalization of silicon substrates, to the specific peptides as such, and to silicon substrates functionalized by the adsorption on their surface of such specific peptides. The present invention is also directed to a process for the preparation of such functionalized silicon substrates, and to articles comprising a functionalized silicon substrate according to the invention.

Silicon surface chemistry is of fundamental technical significance because of the wide-use of this material in various modern technologies. Indeed, silicon is the mostly used semiconductor in micro and nano-electronics, like in transistors and diodes, as it is abundant and cheap. Downscaling is an important demand and miniaturization (to nanometers) in silicon technology is forecasted when biomolecules revealing electronic functionalities are deposited onto silicon. The electronic functionality of numerous molecules can be used in silicon-based devices. However, grafting biomolecules onto silicon in a controlled manner and in nanometer sized monolayers is far to be evident.

Several surface modification methods have been previously reported to render silicon biocompatible and deposit organic molecules onto silicon (J. M. Buriak, Chem. Rev. 2002, 102; S. F. Bent, Surf. Sci., 2002, 500; and D. K. Aswald et al., Anal. Chim. Acta, 2006, 568). Some of these methods are based on silanization (R. Maoz et al., J. Colloid Interface Sci., 1984, 100; J. B. Brzoska et al., Langmuir, 1994, 10; S. R. Wasserman et al., Langmuir, 1989, 5; and N. Tillman et al., J. Am. Chem. Soc., 1988, 110) and condensation of alcoholic groups (G. Clehand et at, J. Chem. Soc. Faraday Trans., 1995, 91). US Patent Application 2009/0036327 also describes a method which renders the 3D inner surface of a porous silicon biochip appropriate for conducting studies on biomolecule interactions. The porous silicon biochip initially having Si—H surface is first silanized, and then coated with an intermediate moiety to minimize non-specific binding molecules. However, these approaches lack of any control on the extent of surface modification and lead to unwanted polymerization, and also a lack of specific surface recognition.

Electrochemical grafting that requires a charged electrode in the vicinity of the surface was also described in order to produce very thin organic films (of about 50 nm) and/or monolayer patterns on silicon (D. K. Aswal et al., Physica E 2009, 41). However, this method works only in the presence of certain electrolytes that are not always compatible with the biomolecules to be grafted onto the silicon.

U.S. Pat. No. 6,248,539 describes the detection of small molecules via the wavelength shifts in the reflectometric interference spectra of porous silicon, the method implemented requiring a previous oxidation step.

U.S. Pat. No. 6,358,613 discloses a method for forming a covalently bound monolayer on silicon surfaces comprising contacting a silicon substrate with an alkene or alkyne in the presence of a solvent-soluble Lewis acid. However, this method is a chemical surface modification way presenting no surface recognition properties.

US Patent Application 2005/0266045 disclosed a biomaterial comprising derivatized porous silicon. To increase its stability the porous silicon was derivatized by hydrosilylation, said metallic-solution mediated exothermic catalytic process taking place in several hours and leading often to metal residues on the treated surface. The method provides a monomolecular layer covalently bound to the silicon surface. However, the hydrosilation method lacks surface recognition properties.

US Patent Application 2008/0242552 discloses the use of phage display technique for selecting crystal-binding peptides with binding specificity including crystals of Group III-V or II-VI semiconductor.

Hence, it appears that none of the methods of the prior art provides a satisfying solution neither in terms of control of the extent of surface modification, nor in terms of selectivity and ease of implementation.

The present invention overcomes the inadequacies and disadvantages of the state of the art by providing a new way for selective functionalization of silicon substrates via surface modification by adsorption of specific peptides that can specifically and directly recognize the silicon, without requiring the use of masks. Indeed, the specific peptides of the invention are directly and simply adsorbed onto the surface of silicon due to their affinity for this material, the proposed functionalization method being thus easy-to-use.

The silicon substrates of the invention also go beyond the state of the art in terms of sensitivity and limit of detection due to the ordered array of molecules assured by the peptides. Besides, the method of the invention solves the interface problems encountered when an organic molecule is adsorbed onto a silicon surface, and thus overcomes the problem related to the unwanted polymerization and denaturation of capturing molecules.

The invention solves the problems of the prior art by providing a novel method to functionalize silicon via peptides revealing specific recognition for this semiconductor, the silicon substrates of the invention being an easy solution for printing molecular monolayers onto silicon devices in hybrid nanoelectronics.

The first object of the present invention concerns the use of a peptide consisting of 5 to 30 amino acid residues, preferably 8 to 15 amino acid residues, and most preferably 12 amino acid residues, said peptide comprising an amino acid sequence selected from LLADTTHHRPWT (SEQ ID NO: 1), SPGLSLVSHMQT (SEQ ID NO: 2), and the sequences presenting at least 80% identity, preferably 95 to 99% identity, and more preferably 98 to 99% identity, with SEQ ID NO: 1 or SEQ ID NO: 2, for the functionalization of silicon substrate.

According to a preferred embodiment, the first object of the invention concerns the use of a peptide consisting of a sequence selected from SEQ ID NO: 1 or SEQ ID NO: 2.

The term "identity" refers to sequence identity between two peptides. Identity can be determined by comparing a position in each sequence which may be aligned for purposes of comparison. Various alignment algorithms and/or programs may be used to calculate the identity between two sequences, such as BLAST (Altschul et al., NAR, 1997, 25, 3389-3402). Thus, the invention also includes the use of any functional derivative of the peptides as defined above, comprising one or more modifications which do not affect substantially the activity of the initial peptides. Such modifications include for example: addition and/or deletion and/or substitution of one or more amino acid residue in the peptide chain, and/or replacement of one or more amino acid side chain by a different chemical moiety, and/or protection of the N-terminus, the C-terminus, or one or more of the side chain by a protecting group, and/or introduction of double bonds and/or cyclization and/or stereospecificity into the amino acid chain. Since all the variations are known in the art, it is submitted that a person skilled in the art will be able to produce, test, identify and select other peptides according to the present invention.

For instance, it is possible to substitute amino acids by equivalent amino acids. The term "equivalent amino acid" is used herein to name any amino acid that may substitute for one of the amino acids belonging to the initial peptide structure without modifying the activity of the initial peptide structure. These equivalent amino acids may be determined by their structural homology with the initial amino acids to be replaced. As an illustrative example, it should be mentioned the possibility of carrying out substitutions like, for example, leucine by valine or isoleucine, aspartic acid by glutamic acid, glutamine by asparagine, or asparagine by lysine, it being understood that the reverse substitutions are permitted in the same conditions.

A second object of the present invention relates to a peptide as such consisting of 5 to 30 amino acid residues, preferably 8 to 15 amino acid residues, and most preferably 12 amino acid residues, said peptide comprising an amino acid sequence selected from LLADTTHHRPWT (SEQ ID NO: 1), SPGLSLVSHMQT (SEQ ID NO: 2), and the sequences presenting at least 80% identity, preferably 95 to 99% identity, and more preferably 98 to 99% identity, with SEQ ID NO: 1 or SEQ ID NO: 2.

In a preferred embodiment, the peptide of the invention consists of a sequence selected from SEQ ID NO: 1 or SEQ ID NO: 2.

The Si-specific peptides of the invention can be synthetized in the needed quantities by standard biochemical procedures, and then used to functionalize silicon for various applications.

Another object of the invention is a silicon substrate functionalized by the adsorption on its surface of a peptide as defined according to the invention.

Advantageously, the silicon substrate of the invention is a porous silicon substrate having pores diameters greater than 15 nm, and preferably ranging from 15 to 200 nm.

In a preferred embodiment, the peptide adsorbed on the surface of the silicon substrate is covalently coupled at one end to a biological ligand selected from an antibody, a receptor protein, DNA, RNA, or their single strands. The peptide adsorbed on the surface of the silicon substrate may also serve as linker for organic molecules, drugs (when used for drug delivery), and also as linker for biological markers of various diseases such as cancers or inflammatory, or of allergenic proteins for allergy diagnosis in human serum.

The silicon substrate of the invention can be a n-doped silicon substrate or a p-doped silicon substrate. Advantageously, when the silicon substrate is a n-doped silicon substrate it is functionalized by the adsorption on its surface of a peptide comprising SEQ ID NO: 1, and when the silicon substrate is a p-doped silicon substrate it is functionalized by the adsorption on its surface of a peptide comprising SEQ ID NO: 2.

A process for the preparation of a functionalized silicon substrate according to the invention is another subject of the invention. The process of the invention comprises at least the step of contacting a silicon substrate with a peptide as defined according to the invention, the peptides being adsorbed on the silicon substrate.

The process of the invention may also comprise a covalently coupling step of a biological ligand selected from an antibody, a receptor protein, DNA, RNA, or their single strands, at one end of the peptide.

A final object of the invention is an article comprising a silicon substrate according to the invention. Preferably, said article is selected from: microelectronic devices, biomaterials, and optical or electrical biosensors.

Microelectronic Devices:

The invention concerns microelectronic devices as it provides a user-friendly method to passivate silicon and/or deposite organic molecules exhibiting nanoscale electronic functionalities in a highly controlled way. In this application, the peptides can serve as binding linkers of molecules presenting conductivity, said conductive molecules being conductive polymers such as polyacetylenes, polypyrroles, polythiophenes, polyanilines, poly(p-phenylene sulfides) and poly(p-phenylene vinylenes), or conducting biomolecules such as proteins containing metallic ions like ferritin proteins and hemeproteins (hemoglobin) containing iron, or conducting biomolecules which are rendered artificially conductive by grafting onto them metallic nanoparticles such as silver or gold. Coupling biomolecules to silicon might provide promising applications based on the electronic functionality of these molecules in silicon based devices.

Biomaterials:

The invention also provides a novel biofunctionalizing method via peptide-linkers that reduces the toxicity (which is primordial for biomedical applications), and confer biocompatibility and stability to the silicon substrate. The porous silicon substrates functionalized with the peptides of the invention is further modified with ligands or a peptide comprising a RGD (Lysine (R) Glycine (G) Aspartic Acid (D)) sequence, which can enhance cell adhesion on porous silicon scaffold for biomaterial applications. Furthermore, peptide-capping ligands confer protein-like properties to silicon nano-particles (SiNp) with better solubility, stability and molecular recognition properties. The peptides can be used to load active molecules in silicon nano-particles for drug delivery applications (use as carriers for drug delivery), and offer numerous possibilities in terms of self-assembly of silicon nano-particles.

Optical or Electrical Biosensors:

The invention is also related to the surface modification of silicon for optical or electrical biosensors with porous silicon structures, or any silicon based devices like field effect transistors. In this application, the specific peptides are used to functionalize porous silicon structures that have been proved to be ideal scaffolds for detection and identification of biological substances. Optical or electrical biosensing is one of the fastest growing research areas: analyte recognition and detection can be envisaged based on the perturbation of the electro-optical properties of the silicon substrate. Electrochemically etched porous silicon (PSi) devices like porous silicon micro-cavity resonators exhibit interesting intrinsic optical properties for biosensing. The micro-cavity structure is highly sensitive to coupling biomolecules, which can be sensed by optical reflectivity to reveal refraction index change within the photonic porous silicon structure. To avoid unwanted protein denaturation in contact with the silicon surface it must be first functionalized with linkers although providing control on the deposition area.

In other biosensing applications, peptides can be modified at one end by any kind of ligands, like antibodies, to be used to capture the corresponding receptors. These receptors can be those of cell membranes, and in this case the peptide-ligand functionalized silicon surface will serve as a modified substrate promoting cell adhesion. The Si-specific peptide can be modified also to bind nucleic acids DNA, RNA or their single strands to target then the complementary strands via hybridization, leading to a sensor detecting bacteria.

Another biosensing application might be the elaboration of multiplexed sensing (i.e. a biosensor that monitors a number of target molecules at the same time) for complex body fluids (blood, urine, lymphatic liquid, saliva) via porous silicon micro-cavities functionalized by peptides modified at one end by several different molecules, like biomarkers of different diseases such as interleukin and matrix metalloproteinase proteins in saliva, or like glucose or various ions such as potassium and sodium. A multiplexed sensor functionalized by peptides modified at one end by specific antibodies can also, for example, detect allergenic proteins such as human immunoglobulin, peanut lectin and lactoglobulin, for allergy diagnosis in human serum.

In addition to the above provisions, the invention also comprises other provisions which will become clear from the description which follows, which refers to examples illustrating the performances of the silicon substrates of the invention, and also to the attached drawings in which:

FIG. 1 represents the mass spectra of the SPGLSLVSH-MQT peptide (SEQ ID NO: 2) on a MALDI plate (FIG. 1a)) and the mass spectra of the functionalized p+-Si substrate (FIG. 1b)).

Figure 2:
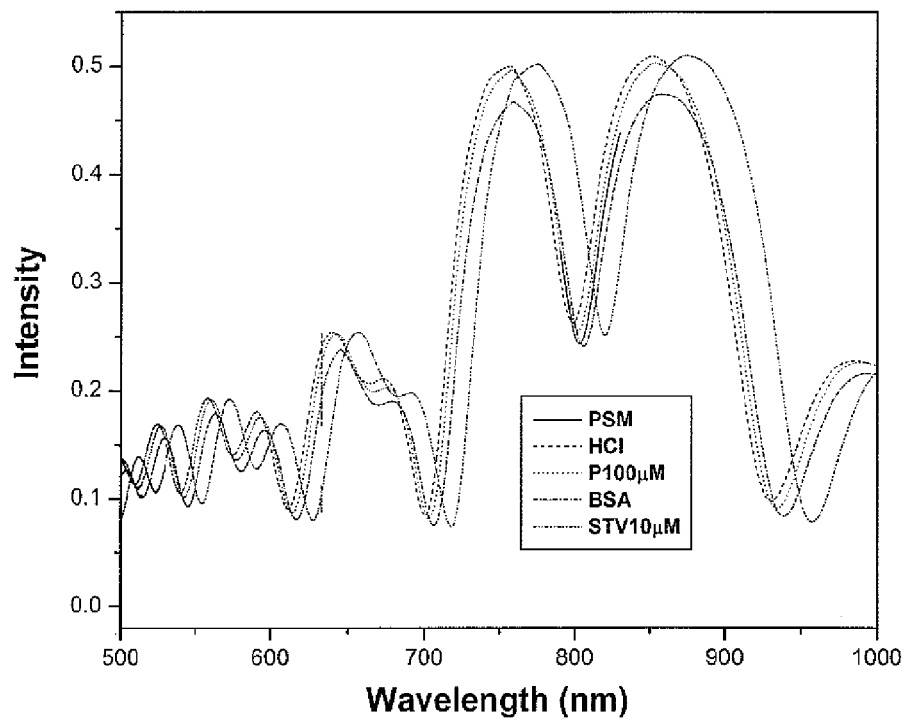
Figure 2:
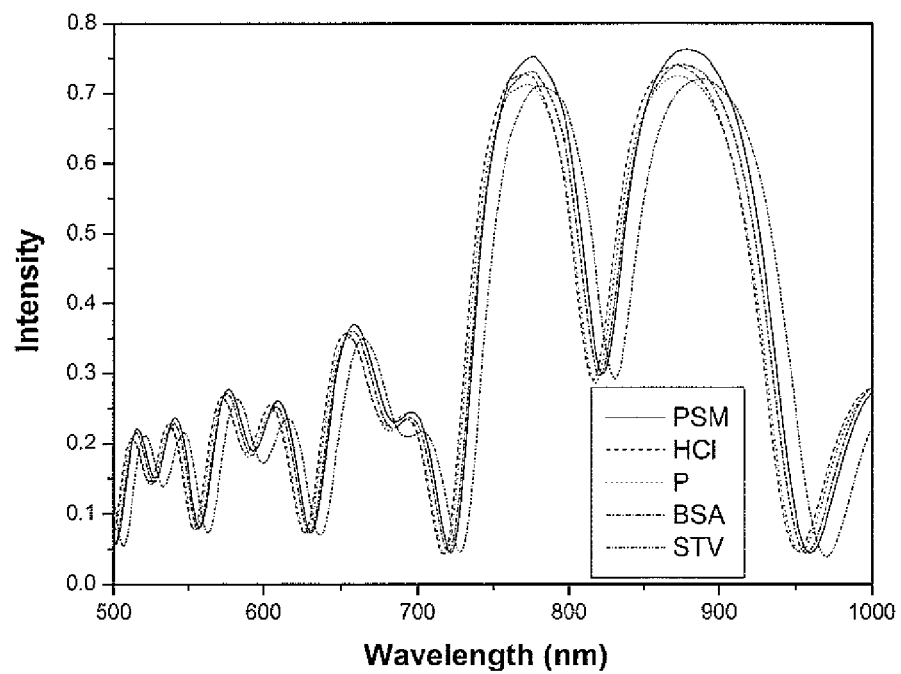
Figure 3:
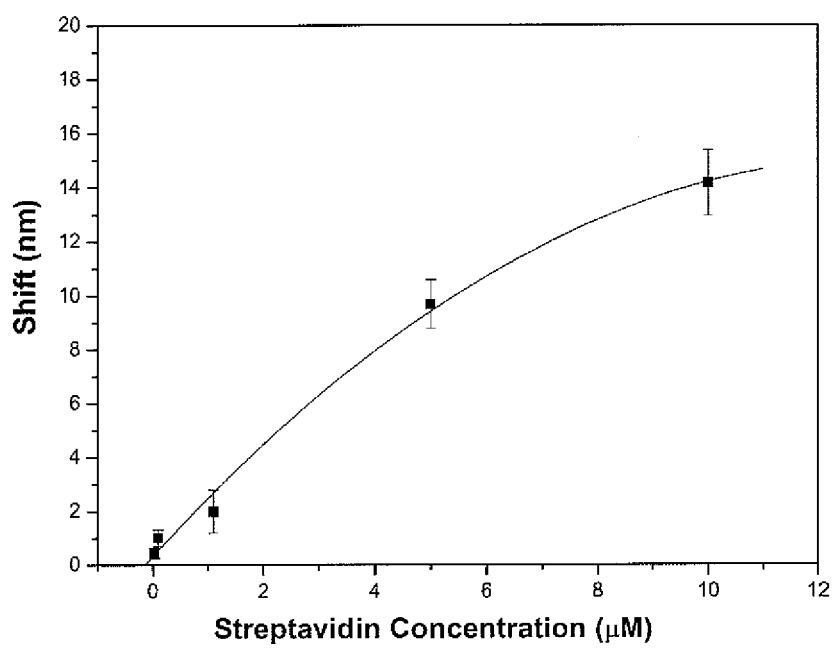
Figure 4:
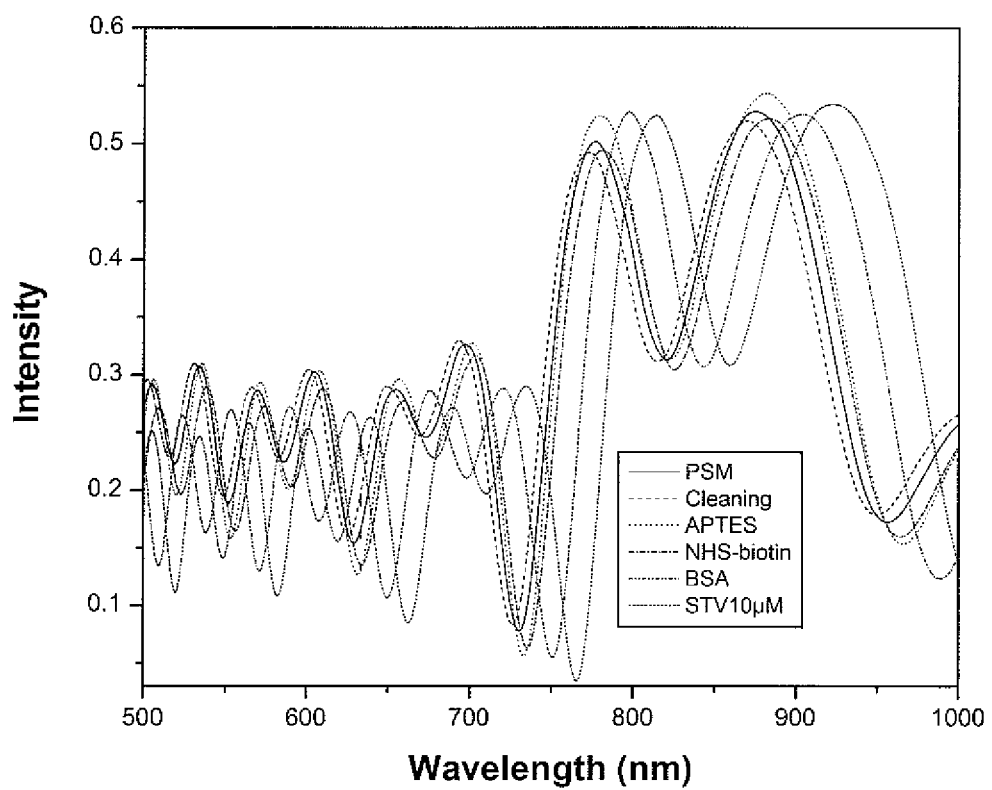
Figure 5:
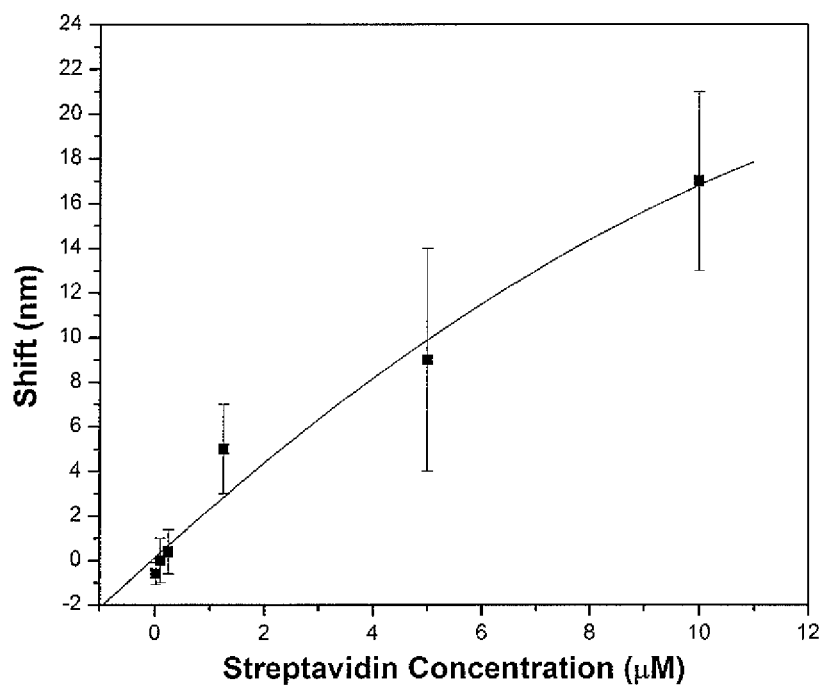
Figure 6:
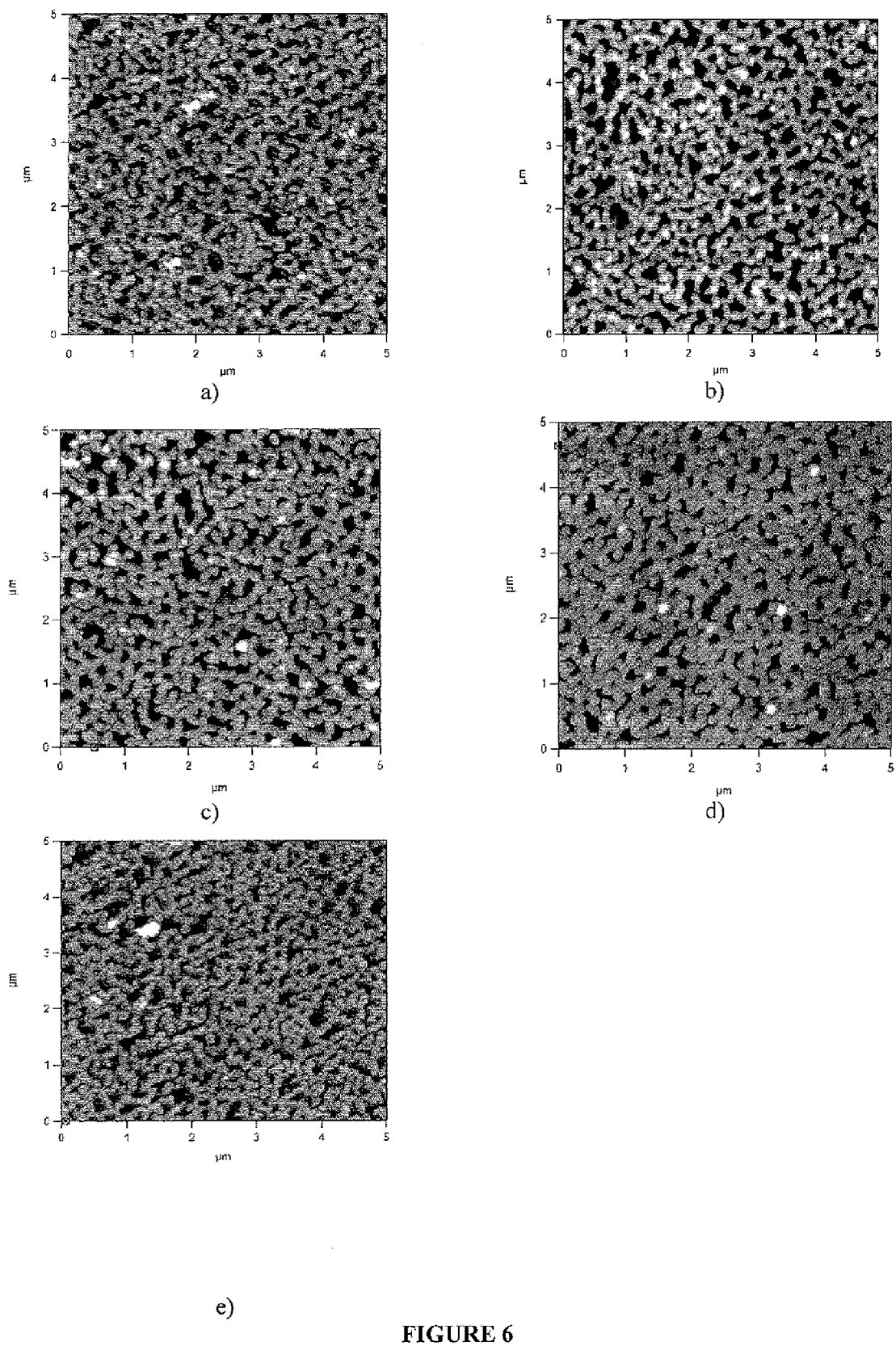
Figure 7:
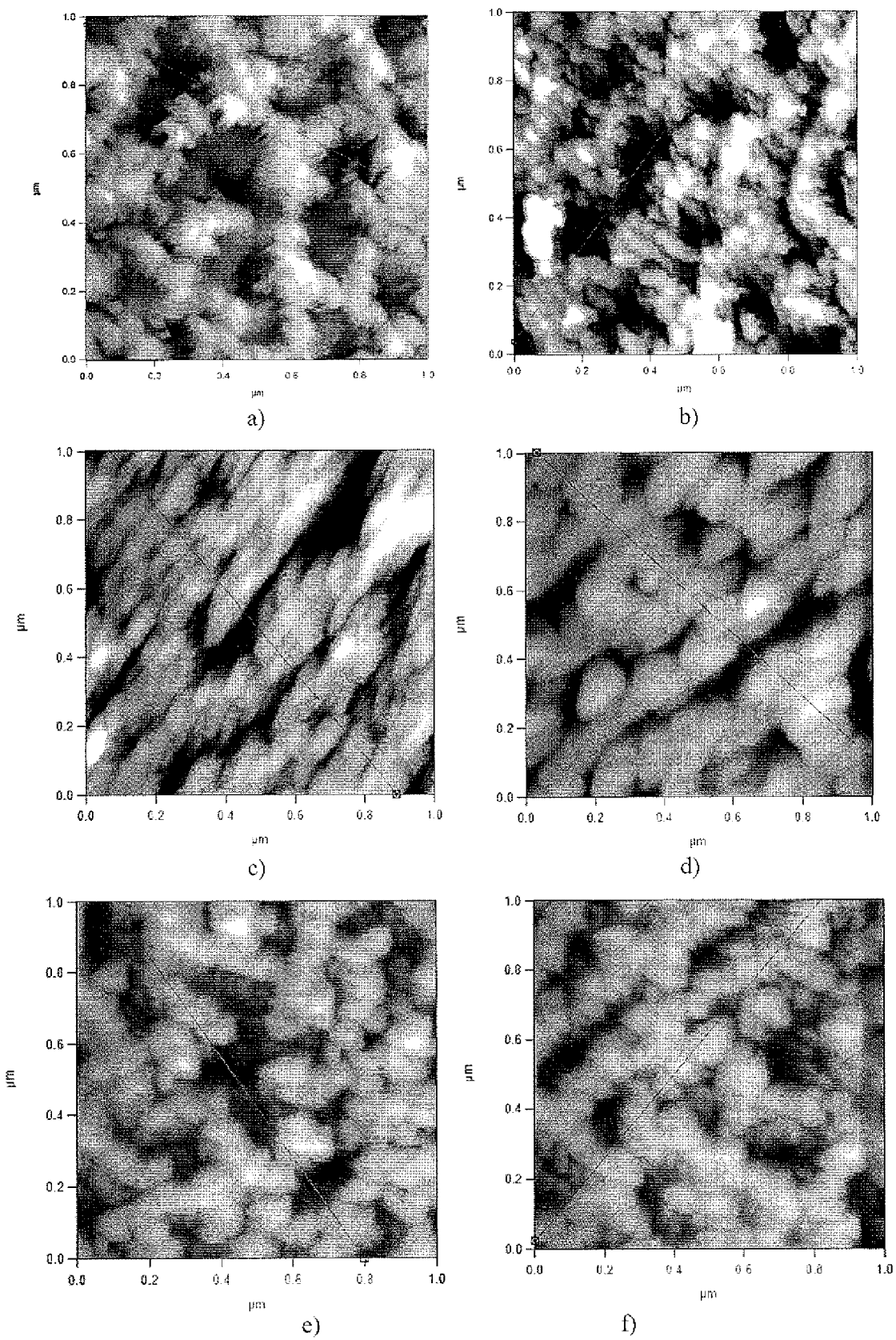
Figure 8:
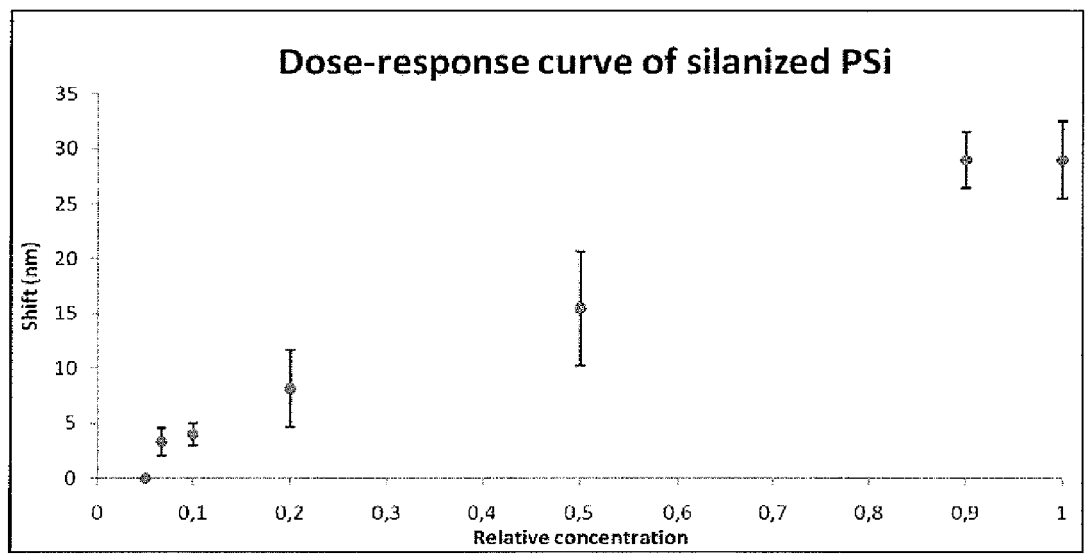
Figure 9:
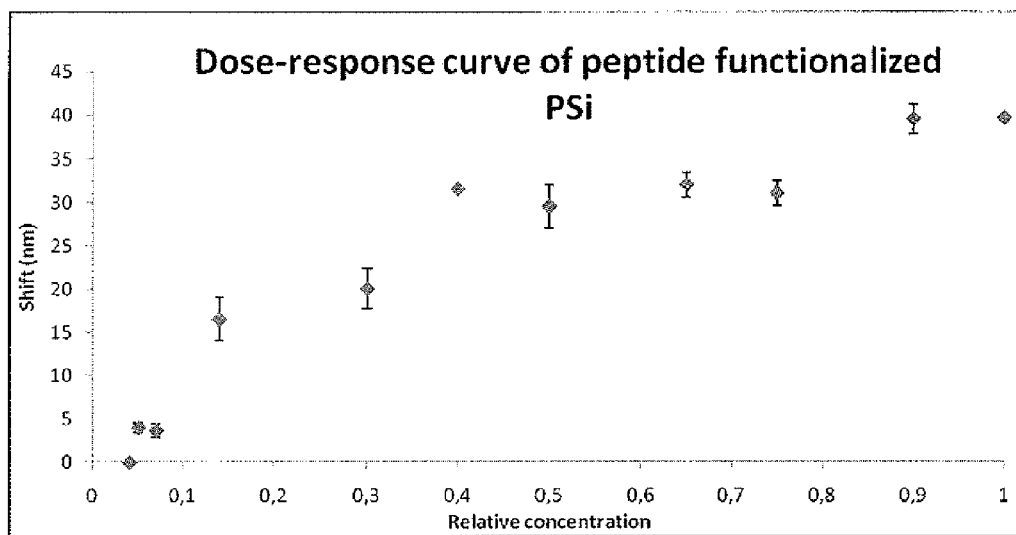
Figure 10:
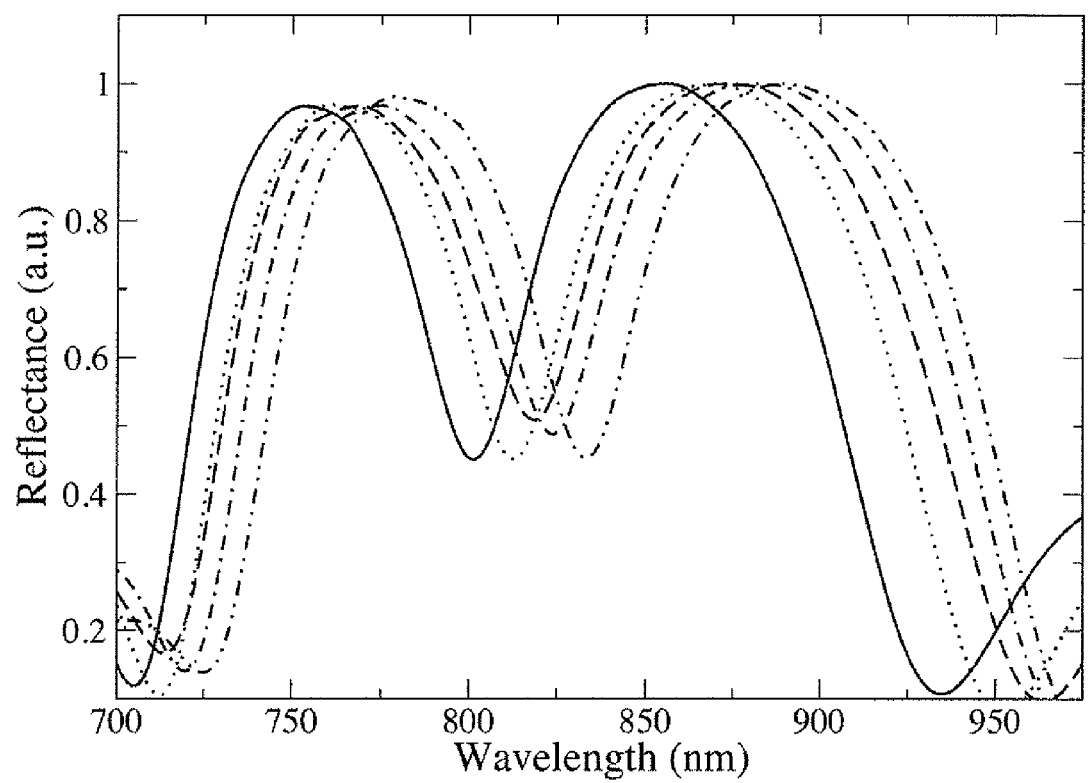
Figure 11:
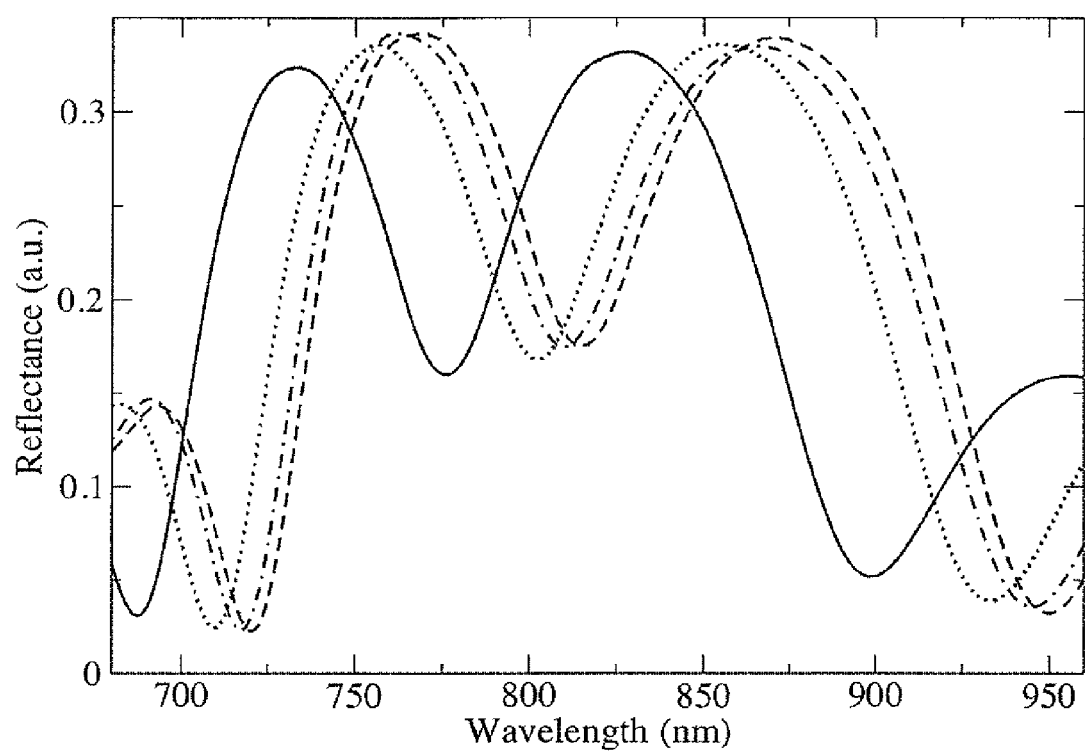

FIG. 2 represents the reflectance spectra of porous silicon micro-cavity substrates (PSM) recorded at different steps of the peptide-functionalization, for a streptavidin (STV) concentration of 10 μM (FIG. 2a)) and for a streptavidin (STV) concentration of 5 μM (FIG. 2b)): after desoxydation (HCL), after adsorption of biotinilated peptide (P), after adsorption of bovine serum albumine (BSA), and after capturing streptavidin (STV), FIG. 3 shows the dose-dependant curve of the peptide-functionalized porous silicon micro-cavity substrates (PSM) devices for different concentrations of captured streptavidin (STV) molecules, FIG. 4 represents the reflectance spectra of porous silicon micro-cavity substrates (PSM) recorded at different steps: after adsorption of (3-aminopropyl) triethoxysilane (APTS), after adsorption of NHS-biotin, after adsorption of bovine serum albumine (BSA), and after capturing streptavidin (STV), FIG. 5 represents the dose-dependent response of the APTES-silanized porous silicon micro-cavity (PSM) devices for different concentrations of captured streptavidin (STV) molecules, FIG. 6 shows the surface topography of the a) bare porous silicon micro-cavity substrate (PSM), b) PSM after deoxidation step, c) PSM modified with 100 μM biotinylated peptide, d) PSM modified with 0.1% BSA, and e) PSM modified with 10 μM streptavidin (STV), as recorded by AFM in air and tapping mode, FIG. 7 shows surface topography of porous silicon micro-cavity substrate (PSM) modified with: a)-b) 100 μM biotinylated peptide, c)-d) then 0.1% BSA, e)-f) and finally 10 μM of streptavidin (STV), as recorded by AFM in air and tapping mode, FIG. 8 shows the dose response curve of porous silicon micro-cavity substrates (PSM) functionalized with silane-glutaraldehyde (GTA) chemistry, and FIG. 9 shows the dose response curve of porous silicon micro-cavity substrates (PSM) functionalized with the peptide method, FIG. 10 represents the reflectance spectra of a porous silicon micro-cavity (PSM) device recording at different steps: at etched, after silanization, after glutaraldehyde (GTA) coupling, after anti-MMP-8 binding, and finally after MMP-8 capture, for an antibody and enzyme concentration of 10 $\mu g \cdot mL^{-1}$, FIG. 11 represents the reflectance spectra of a porous silicon micro-cavity (PSM) device recording at different steps: at etched, after peptide binding, after anti-MMP-8 binding, and finally after MMP-8 capture, for an antibody and enzyme concentration of 100 $ng \cdot mL^{-1}$.

EXAMPLES

The specific peptides of three silicon wafers: a silicon substrate doped with donor impurities, known as n-type (n+-Si), and two silicon substrates doped with acceptor impurities, known as p-type (p-Si and p+-Si), were studied.

Peptide adhesion to the silicon substrate was assessed via MALDI-TOF/TOF mass spectrometry.

The peptides used in the examples were biotinilated, and then used as linkers to capture streptavidin (STV). The detection was monitored via the photonic resonance of the porous silicon micro-cavity. More specifically, the specific biotinilated peptide of the p+-Si was used to functionalize the porous silicon, and streptavidin (STV) molecules were then detected via reflectometric interference spectra as shifts in the resonance peak of the cavity structure.

The results obtained with the silicon substrates of the invention have been compared to those obtained with other silicon substrates: oxidized porous silanization was also performed with (3-aminopropyl) triethoxysilane (APTES) to capture NHS-biotin, and then detect streptavidin (STV). High resolution images of all the functionalization steps were provided by Atomic Force Microscopy (AFM).

Peptide adhesion was assessed via MALDI-TOF/TOF mass spectrometry.

Silicon Substrates:

n- and p-doped silicon are standard wafers grown by the Czochralski method (A. Phys. Chem., 1918, 92, 219-221). n-type and p-type doping impurities are phosphorous and boron respectively with doping level ranging from $10^{15}$ $cm^{-3}$ for p-Si to $10^{19}$ $cm^{-3}$ for n+-Si and p+-Si. Before use, the silicon wafer was cleaved to extract 5×5 $mm^2$ samples that were then carefully cleaned by successive treatment with trichloroethane, acetone, methanol, rinsed in de-ionized water, and then dried under nitrogen. In order to remove the native oxide, samples were deoxidised with dilute hydrofluoric acid (HF) (2.5 mL HF at 40% in 22.5 mL of water) during 1 minute, and then immersed in deionised water and finally dried under nitrogen.

MALDI-TOF/TOF Mass Spectrometry on Peptide-Functionalized Silicon:

Once cleaned and deoxidized, the samples were incubated during 2 hours in a solution of a PBST in which 90 μM of a peptide is diluted, followed by a thorough rinsing step with deionised water, in order to remove buffer traces, unbound and excess of peptide. A matrix solution, i.e. α-cyano-4-hydroxycinnamic acid (αCHCA) (5 mg/mL) in a solvent composed of acetonitrile/$H_2O$/trifluoroacetic acid (50/50/0.1), was then added to the silicon samples and dried for the crystallisation. The samples were fixed to a MALDI plate via a conductor double sided tape. For control experiments, the mass spectra of the peptide was measured when 1 μL of the diluted peptide (90 μM in water) was mixed with 9 μL of the matrix solution and deposited on the stainless steel sample plate. The mass spectra of the matrix deposited onto the silicon surface (without the peptide) was also recorded as a control experiment.

The prepared samples were allowed to air-dry, and then analyzed by a 4800 Plus MALDI-TOF/TOF Proteomics Analyzer (Applied Biosystems, Foster City, Calif., USA) in positive reflector ion mode using a 20 kV acceleration voltage. The YAG laser was operated at a 200 Hz firing rate at a wavelength of 355 nm. Mass spectra were acquired for each measure using 1500 laser shots. The fragmentation of the peptide was also investigated with the MS/MS mode. Acquired spectra were processed using 4000 Series Explorer™ software (Applied Biosystems).

Functionalization of the Porous Silicon:

The porous silicon micro-cavity structures (PSM) were fabricated by a wet electrochemical etching process using highly doped, p-type (boron doped) Si wafers (thickness of 500-550 μm) with a 0.002-0.004 $\Omega \cdot cm^{-1}$ resistivity, and with a crystallographic orientation of (100). The electrolyte consists of hydrofluoric acid (48%), ethanol (98%) and glycerol (98%) in a volumetric ratio of 3/7/1. The anodization time and current density were controlled by a computer interface electronic circuit. Samples were fabricated in dark and freshly etched samples were washed with ethanol and dried with pentane. The structures were fabricated using a current density of 90 $mA \cdot cm^{-2}$ (H for high) and 40 $mA \cdot cm^{-2}$ (L for low). The anodization time of 6.4 seconds and 11.5 seconds, respectively for H and for L, were used for the fabrication of the corresponding dielectric Bragg minors (optical thickness of each layer being one quarter of the wavelength, with wavelength ranging from 740 to 810 nm) with 10 periods.

To minimize salt crystallization in the porous silicon devices while functionalization, the used solvent (PBST and PBS) was diluted 10 times in deionised water (PBST/10, PBS/10). Hence the rinsing step was first made with 500 μL of PBS/10, followed by a washing step with 500 μL deionised water.

The SPGLSLVSHMQT peptide was synthesized by coupling the carboxyl group or C-terminus of one amino acid to the amino group or N-terminus of another using multiple peptide synthesizers. Then, the peptide has been elongated with a (GGGSK) linker to bind a biotin at the C-terminus of the peptide. The obtained final molecule is thus the SPGLSLVSHMQT-GGGSK-biotin.

After the step of deoxidation with diluted chlorhydric acid (HCl) (1/10 in deionised water), the porous silicon sample was incubated in 20 μM or 100 μM of a biotinylated peptide (diluted in PBST/10) during 2 hours, followed by a thorough rinsing step in order to remove unbound and excess of peptide. Then, the sample was incubated in Bovine Serum Albumine (BSA 0.1% in PBS/10) during 1 hour. In the following step, various concentrations of streptavidin (STV) (diluted in BSA 0.1% in PBS/10) were added to porous silicon micro-cavity substrates and let to adsorb during 1 hour, followed by a rinsing step. Drying under nitrogen was performed after each surface modification step for experimental needs. All rinsing steps were made first with PBS/10, and then with deionised water to avoid salt crystal formation.

For comparison, sensing was performed also with porous silicon micro-cavity structures thermally oxidized at 900° C. during 3 minutes, and then silanized with APTES by incubating the sample in 50 of APTES diluted in 950 μL of toluene during 50 minutes. Then, the sample was successively rinsed with toluene, then with 50% ethanol, and finally with deionised water. Samples were then baked at 115° C. for 15 minutes. In the next step, 100 μM of NHS-biotin diluted in dimethylsulfoxide (DMSO) was coupled to the APTES, followed by blocking unspecific binding sites with BSA 0.1% in PBS/10, and then used to capture streptavidin (STV) at various concentrations.

Atomic Force Microscopy (AFM):

AFM images were recorded in air, with an Asylum MFP-3D head and Molecular Force Probe 3D controller (Asylum Research, Santa Barbara, Calif., USA). Images were acquired in tapping mode using silicon, rectangular cantilevers (Olympus Microcantilever, OMCL-AC240TS). Height and phase images were recorded with 512×512 point scans at 1 Hz scan rate. Several scans over a given surface area were performed in order to assure porous silicon micro-cavity reproducible images.

Reflectivity Spectra:

Reflectivity spectra were measured by illuminating the modified samples at normal incidence angle with a tungsten source (Balker 66V) and detecting the reflected beam by means of a silicon diode detector. This spectrophotometer was coupled with a Bruker A 510, 11° Specular Reflection Unit. A spectrum resulting from the accumulation of 100 scans was acquired after each modification of porous silicon with a resolution of 2 $cm^{-1}$, and in a range comprised between 25000 and 9000 $cm^{-1}$.

Selection of the Specific Peptides of the Invention:

Several peptides were selected by implementing a phage display technology using a M13 bacteriophage library (New England Biolabs), performed on the three types of silicon substrates mentioned here-above ((n+-Si), (p-Si) and (p+-Si)) in phosphate-buffered saline solution containing 0.1% TWEEN-20 (PBST), after a previous cleaning and deoxidation with diluted HF. After a stirring of 1 hour at room temperature, the surfaces were washes typically 10 times with PBST to rinse the unbound phages. In the next step, the bound phages were eluted from the surfaces: glycine-HCL (pH=2.2) solution was added during 10 minutes, and then the surface was transferred to a fresh tube and neutralized with Tris-HCL (pH=9.1). Eluted phages from each sample were infected into Escherichia coli ER2738 host bacterial cells and thereby amplified. After three rounds of biopanning, monoclonal phage populations for each surface type were selected and analyzed individually. Finally, 10 phages were recovered and amplified, followed by extraction and sequencing of their DNA that will define the sequence of the expressed peptide.

The sequences of the peptides extracted from the recovered phages are gathered in Table 1.

The http://expasy.org program has been used to calculate the physico-chemical characteristics of the different peptides including the molecular theoretical mono-isotopic molecular mass (MW), the isoelectric point (pI), the instability index (II), the aliphatic index (AI), and the hydropathicity (H).

TABLE 1

Sequences and physico-chemical characteristics of different peptides

| | Selected Peptides (%) | MW | pI | Charge | II | AI | H |
|---|---|---|---|---|---|---|---|
| | $n^+$-Si | | | | | | |
| 3$^{rd}$ cycle | SVSVGMKPSPRP (42.8) | 1240.66 | 11 | +2 | 58.24 | 48.33 | −0.475 |
| 3$^{rd}$ cycle | LLADTTHHRPWT (28.5) | 1446.74 | 6.92 | +1−1 | −9.31 | 73.33 | −0.800 |
| 3$^{rd}$ cycle | GQPLIAHSTKLL (14.2) | 1276.75 | 8.76 | +1 | 11.07 | 138.3 | 0.300 |
| 3$^{rd}$ cycle | FPNPPPMTITMP (14.2) | 1341.65 | 5.52 | 0 | 82.85 | 32.50 | −0.150 |

TABLE 1-continued

Sequences and physico-chemical characteristics of different peptides

| | Selected Peptides (%) | MW | pI | Charge | II | AI | H |
|---|---|---|---|---|---|---|---|
| | | p-Si | | | | | |
| $3^{rd}$ cycle | SVSVGMKPSPRP (75) | 1240.66 | 11 | +2 | 58.24 | 48.33 | -0.475 |
| $3^{rd}$ cycle | GSMSPYVRWYTP (12.5) | 1442.67 | 8.59 | +1 | 123.0 | 24.17 | -0.650 |
| $3^{rd}$ cycle | TLGFRNSDYLYI (12.5) | 1460.73 | 5.50 | +1-1 | 19.45 | 97.50 | -0.092 |
| | | $p^+$-Si | | | | | |
| $3^{rd}$ cycle | SVSVGMKPSPRP (44.4) | 1240.66 | 11 | +2 | 58.24 | 48.33 | -0.475 |
| $3^{rd}$ cycle | SPGLSLVSHMQT (44.4) | 1255.62 | 6.46 | 0 | 39.50 | 89.17 | 0.158 |
| $3^{rd}$ cycle | ANHNKMLQYRQP (11.1) | 1498.75 | 9.99 | +2 | 114.6 | 40.83 | -1.750 |

Signification of the instability index (II) of a peptide: II < 40 predicts a stable peptide, and II > 40 predicts an unstable peptide.
The hydropathicity (H) is calculated as the sum of hydropathy values (J. Kyte et al., J. Mol. Biol., 1982, 157: 105-132) of all the amino acids, divided by the number of residues in the sequence.
For the $n^+$-Si, the adopted specific peptide is the LLADTTHHRPWT, with an apparition frequency of 28.5%.
For the $p^+$-Si, the adopted specific peptide is the SPGLSLVSHMQT with an apparition frequency of 44.4%.

Assessing Peptide Adhesion via MALDI-TOF/TOF Mass Spectrometry:

The affinity of the SPGLSLVSHMQT peptide (named here-after as peptide P) for the p+-Si surface has been evaluated by MALDI-TOF/TOF mass spectrometry. The cleaned and deoxidized p+-Si surface was functionalized with the P peptide followed by the matrix deposition, and measured in the mass spectrometer. In order to determine the exact mass of the peptide P, spectra of the peptide solution (without silicon) was first recorded and represented on FIG. 1a). The obtained mass-to-charge ratio (m/Z) value of 1256.6 is in agreement with the theoretical $[M+H]^+$ mass of the peptide. There is also a small peak of the oxidised peptide with a mass of 1273.5.

When the silicon surface was functionalized with the P peptide, then rinsed with deionised water, peaks in the region of m/Z 1254-1270 were observed and represented on FIG. 1b), indicating the irreversible adhesion of the P peptide onto the surface. The slightly lower values compared to those obtained for the peptide alone are due to the thickness of the silicon substrate.

Streptavidin (STV) Detection via Peptide-Functionalized Porous Silicon Micro-Cavity (PSM) Devices:

As the used PSM substrates are prepared from highly doped p+-Si (with a crystallographic face (100)) wafers, the specific peptide obtained for the p+-Si (100) was used to functionalize PSM. All the functionalization steps were monitored by the reflectance spectra measured as a shift in the interference peak caused by the change in the effective optical thickness of the substrate when molecules are captured by the pores. When compared to the reflectance spectra measured on the bare PSM sample, deoxidation reveals a shift of about 5.5 nm allocating to the effect of opening the pores under acid treatment. Nevertheless, as the overall shape of the spectra is not changing it seems that the structure itself is not attacked during deoxidation. When functionalized with its specific biotinilated peptide at a concentration of 100 μM, the spectra shifts towards the longer wavelengths is observed during the adsorption of BSA, and then the streptavidin (STV) is captured. The addition of 10 μM of streptavidin (STV) onto the PSM leads to a shift of about 14 nm (FIG. 2).

The measurements were performed at various concentrations of streptavidin (STV) and a less concentrated peptide solution (at 20 μM) has also been used to functionalize PSM and to capture the streptavidin (STV) at different concentrations. The measured shifts are gathered in Table 2.

TABLE 2

Shift and concentration of molecules adsorbed on the PSM samples in the peptide-functionalization method as monitored by reflectance spectra

| | $\Delta\lambda_{HCl}$ (nm) | $P_{concen\text{-}tration}$ | $\Delta\lambda_P$ (nm) | $\Delta\lambda_{BSA}$ (nm) | $STV_{concen\text{-}tration}$ | $\Delta\lambda_{STV}$ (nm) |
|---|---|---|---|---|---|---|
| PSM1 | -6.51 | 20 μM | +1.88 | +3.33 | 10 nM | +0.30 |
| PSM2 | -6.51 | 20 μM | +1.88 | +3.33 | 110 nM | +2.31 |
| PSM3 | -6.38 | 20 μM | +2.83 | +3.42 | 1 μM | +2.49 |
| PSM4 | -5.18 | 20 μM | +1.88 | +3.24 | 10 μM | +17.6 |
| PSM5 | -6.48 | 100 μM | +1.23 | +4.47 | 25 nM | +0.46 |
| PSM6 | -5.61 | 100 μM | +2.86 | +3.61 | 100 nM | +1.01 |
| PSM7 | -6.48 | 100 μM | +1.23 | +4.47 | 1.1 μM | +2.00 |
| PSM8 | -6.66 | 100 μM | +1.72 | +3.02 | 5 μM | +9.68 |
| PSM9 | -4.75 | 100 μM | +3.33 | +3.48 | 10 μM | +14.16 |

There is no considerable difference in the obtained shifts for both concentrations of 20 and 100 μM of peptide. In fact, the adhesion of peptides on silicon has been reported to be saturated at 20 μM. Adsorption of BSA results in a shift of $\Delta\lambda_{BSA}$=3-4 nm, rather constant for all the measurements. On the contrary, a gradual increase in the $\Delta\lambda_{STV}$ is observed when streptavidin (STV) is captured at increasing concentrations. The lowest tested concentration was 10 nM of streptavidin (STV) leading to a shift of 0.30 nm.

The dose-response curve was also represented on FIG. 3. The polynomial line fit of the experimental result shows that detection of the streptavidin (STV) at high concentrations starts to be saturated (16-17 nm shift). It is known that the minimum and maximum detection limits are affected by the porous silicon itself (i.e. fabrication, porosity, the method of functionalization and the size and type of the detected protein). The Quality (Q) factor of the device defined as $Q=\lambda/\Delta\lambda$ play also an important role, thus it is crucial to keep a good Q factor before and after functionalization and detection. A high Q factor value increases the ability to resolve small wavelength shifts. The Q factor of the PSM is of about 40, due to the high porosity of these structures.

Streptavidin (STV) Detection via Silanized PSM Devices:

The functionalization of PSM via APTES silanization chemistry as witness was also performed, in order to compare the detection limit of streptavidin (STV) sensing with that obtained via the peptide-functionalized devices of the invention. The first spectrum corresponds to the oxidised PSM, and is followed by the spectra recorded after the cleaning step, which lead to a shift of about 4 nm (FIG. 5). Silanization produces a shift of about 9 nm, and the binding of the NHS-biotin (100 μM) shifts again with $\Delta\lambda_{NHS-biotin}$=+1.6 nm. Adsorption of BSA leads to a shift of about 18 nm, and finally capturing of 10 μM concentrated streptavidin (STV) shifts about 16.55 nm. As usual, all rinsing was performed in two steps first by PBS/10, and then by deionised water.

TABLE 3

Shift and concentration of molecules adsorbed on the PSM samples by the APTES functionalization method monitored by reflectance spectra

|  | $\Delta\lambda_{cleaning}$ (nm) | $\Delta\lambda_{APTES}$ (nm) | $\Delta\lambda_{NHS-biotin}$ (nm) | $\Delta\lambda_{BSA}$ (nm) | $STV_{concentration}$ | $\Delta\lambda_{STV}$ (nm) |
|---|---|---|---|---|---|---|
| PSM1 | −4.86 | +12.27 | +0.97 | +19.08 | 25 nM | −0.58 |
| PSM2 | −4.8 | +13.79 | +2.8 | +2.4 | 25 nM | −0.99 |
| PSM3 | −4.86 | +12.27 | +0.97 | +19.08 | 100 nM | 0 |
| PSM4 | −4.79 | +8.79 | +2.19 | +27.58 | 100 nM | −1.39 |
| PSM5 | −3.99 | +14.59 | +1.2 | +10.19 | 250 nM | +0.39 |
| PSM6 | −3.99 | +14.59 | +1.2 | +10.19 | 1.25 μM | +5.39 |
| PSM7 | −3.99 | +14.59 | +1.2 | +10.19 | 5 μM | +13.59 |
| PSM8 | −5.19 | +10.39 | +1.4 | +22.39 | 5 μM | +4.09 |
| PSM9 | −5.37 | +8.79 | +1.6 | +18.19 | 10 μM | +16.55 |

Table 3 gathers the measured shifts in the reflectance spectra of PSM after each functionalization step for different experiments made by varying the streptavidin (STV) concentration. The shift induced by the APTES-silanization varies from +8.79 nm to +14.59 nm, which might suggest that APTES molecules adsorb in different quantities and/or tend to aggregate. Large oscillations in the $\Delta\lambda_{BSA}$ values obtained after BSA adsorption can also be observed. These values are much higher than those obtained in the peptide functionalization method, where an average shift of about 3 nm was recorded. This important difference indicates that the used peptide covers almost completely the inner surface of the porous silicon micro-cavity substrate (PSM) excluding thereby BSA binding, whereas silanisation fails to do this. The difference in the two functionalization methods has its consequence also in the subsequent molecular sensing, as when capturing the streptavidin (STV) at small concentration (25-100 nM) small shifts have been recorded. This observation can be interpreted by the removal of a small BSA amount of the surface when incubating the sample in the streptavidin (STV) solution, and followed by rinsing. The procedure can remove some excessive BSA that is not bond in an ordered manner, by forming a rough layer which also explains the large shift produced when BSA is adsorbed. It is only with a 250 nM concentrated streptavidin (STV) that we obtain a small shift of +0.39 nm.

To determine the limit of detection for the two differently functionalized PSM devices we have performed statistical analysis of measured data. The limit of detection (LoD) for steptavidin (STV) was calculated from the formula LoD=3σ/s, where σ is the relative standard deviation of the background and s is the slope of the regression line defined by the measurements. The obtained LoD values, the relative standard deviation (σ%) and the correlation coefficient ($R^2$) for the differently functionalized devices are listed in Table 4.

TABLE 4

The calculated limit of detection (LoD) values, the relative standard deviation (σ%), the correlation coefficient ($R^2$) and the regression equations for the differently functionalized devices

| Streptavidin (STV) on Psi functionalized with | LoD (nM) | σ% | $R^2$ | Regression equation |
|---|---|---|---|---|
| 20 μM biot-peptide | 41.4 | 2.21 | 0.9907 | y = 0.0016x + 1.0889 |
| 100 μM biot-peptide | 340.8 | 15.9 | 0.9725 | y = 0.0014x + 0.8884 |
| APTES-biotin | 885.8 | 50.18 | 0.8309 | y = 0.0017 − 0.0545 |

The results show that the lowest detection limit is obtained via the PSM devices. Moreover, the optimal peptide concentration (20 μM) can be determined for streptavidin (STV) detection via PSM devices. When higher peptide concentration is used, the background σ increases, leading to higher LoD value and this effect is even more accentuated for the silanized PSM devices.

The results demonstrate the importance of surface modification of PSi based devices for sensing: peptide functionalization leads to a detection limit that is 21 times lower than that obtained from silanized PSM. Furthermore, important errors on the STV sensing dose-response curve (FIG. 5) from silanized PSM devices, especially at higher concentrations (greater than 1 μM), can be noted. Sensing with peptide-functionalized PSM is very reproducible, as shown by the low error bars on the dose-response curve presented in FIG. 3.

Moreover, when PSM is silanized, in some experiments the amplitude of the spectra is lowered and its form is also slightly modified, which can be attributed to the scattering losses from the possibly cracked surface while drying process after silanization. Therefore, when continuing with further adsorption after silanization, it is difficult to obtain reproducible shifts and valuable information at small protein concentrations. In contrast, in experiments performed with peptide-functionalized PSM, all spectra obtained are exactly the same, indicating that the adsorption of peptide does not affect microcavity structure.

Morphological Studies on Functionalized PSM Devices:

The morphological study on the different functionalization steps was performed by atomic force microscopy leading to valuable information on the surface modification of porous silicon micro-cavity substrates (PSM). First, the images of the bare sample (before cleaning) were recorded in air and tapping mode (FIG. 6a)). The increasing of porosity (more and bigger pores) after the HCl cleaning step can then be noticed (FIG. 6b)). When the biotinylated peptide is added to the sample, the formation of a thin layer covering the entire surface is observed (FIG. 6c)) also from the profilometric section. After incubation with BSA, the formed layer is highly ordered (FIG. 6d)), and pores become smaller and less deep than those after peptide adsorption (FIG. 6c)). Finally in the last step, FIG. 6e) evidences the formation of a streptavidin (STV) layer: the profilometric section shows that the layer becomes thicker.

When imaging at higher resolution, organization of molecules can be observed on the surface (FIG. 7). After adsorption of biotinilated peptide, the formation of a molecular layer with a thickness that is never exceeding 5 nm can be observed (FIG. 7a) and FIG. 7b)). The small scale images also evidence that the BSA molecules bind onto the biotin in an ordered way (FIGS. 7c) and 7d)). Finally, when streptavidin (STV) is captured, the molecular layer around the pores becomes thicker but still not exceeding few nanometers (FIG. 7e) and FIG. 7f)). The AFM images demonstrate the formation of ordered protein monolayers onto the porous silicon surface when peptide functionalization has been performed, whereas polymerisation and formation of aggregates has been observed when porous silicon substrates were functionalized via silanization chemistry.

The sensors modified by the adsorption of a peptide according to the invention presents a higher sensitivity than the traditional silanized sensors. The results obtained demonstrate that the streptavidin (STV) sensing with peptide-functionalized porous silicon micro-cavities is 21 times better compared to those performed with the devices functionalized by the common silanization method. Moreover, the reproducibility of the reflectance measurements carried on peptide-functionalized PSM devices according to the invention, as well as the intact state of the micro-cavity structure after all steps of bio-functionalization, contrary to the observations made on APTES-silanized porous silicon devices, were also revealing. High resolution atomic force microscopy images prove the formation of ordered nanometer sized molecular layers when the peptide-route functionalization according to the invention is performed.

Photosynthetic Bacterial Reaction Centres Adsorbed on Porous Silicon:

The photosynthetic reaction centre (RC) is an important protein performing light energy transduction into chemical energy. The first step in the conversion of light to chemical energy is the formation of a chemical potential of charge pair, which is the condition of creating trans-membrane chemical potential of hydrogen ions. Even though the reaction centre protein, also called the "nature's solar power stations" or the "nature's solar comb", ensures the energy for the whole earthly life, including the fossil fuels. Its size represents only nanometers in the cells (about 10 nm) and it works only in nano-efficiency (one photon makes only one charge separation). It would be a real challenge to harness the energy conversion of reaction centres as the quantum efficiency of their movement is 100% for example in the use of the solar energy. Combining reaction centres with semiconductor type materials could eventually stabilize them and optimize the charge separation process within the protein necessary for electron transport. Immobilizing RC onto a porous substrate might also be a good way to produce a highly concentrated RC matrix. Proper functionalization of porous silicon (PSi) before RC linking will also contribute to maintain the efficiency of the light conversion and to avoid the reduction of the efficiency of the biological system enlarging its stability and extending the use possibilities.

In this example, the binding of bacterial reaction centre on porous silicon has been performed via two methods:
- covalent binding via silane-glutaraldehyde (GTA) chemistry, and
- after functionalization with peptides revealing high binding affinity to Si material. Adsorption of RCs onto porous silicon was monitored via the red shift of the specular reflectance spectra of the used PSi microcavities due to refractive index changes when molecular binding occurs. The measured shift depends on the amount of immobilised reaction centre. More molecules are bound, more important the shift in the reflectance spectra is. FIGS. 8 and 9 illustrate the measured spectral shifts in function of RC concentration when RC binding is performed via covalent linking (FIG. 8) and via peptide binding with the Si-specific SPGLSLVSHMQT peptide (FIG. 9). In both graphs the relative concentration of 0.1 corresponds to 600 nM. The obtained dose response curves indicate the lowest detectable concentration and the sensing resolution of the PSi structures. We have demonstrated that when bound via the SPGLSLVSHMQT peptide, RC capture by porous silicon micro-cavity (PSM) produces larger spectral shifts compared to those obtained with the porous silicon micro-cavity substrates (PSM) modified via silane-glutaraldehyde (GTA) chemistry. This strongly suggests that the peptide linker offers better binding conditions for the bacterial reaction centres.

Matrix Metalloproteinase Sensing via Porous Silicon Micro-cavity Devices Functionalized with Human Antibodies:

This example relates to the detection of matrix metalloproteinases, the major enzymes that degrade extracellular matrix proteins and play a key role in diverse physiological and pathological processes, including embryonic development, wound repair, inflammatory diseases and cancers.

Porous silicon micro-cavity substrates (PSM) were used as support material for specific sensing of matrix metalloproteinases (MMPs). In this example, the collagenase-type MMP-8, which is an inflammatory marker in gingival fluid for predicting tooth movement during orthodontic treatment, is detected. As presence of MMP-8 in saliva is directly related with the tooth movement during orthodontic treatment, monitoring the MMP-8 variation is primordial. Use of Psi porous scaffolds as easy-to-use, sensitive, robust and inexpensive biosensor may lead to promising applications for in situ detection of MMP-8.

Porous silicon micro-cavity substrates (PSM) were used for sensing of low concentrations (down to 100 ng/mL) of MMP-8. The PSM devices were functionalized according to two different functionalization methods:

Method 1: Silanization of PSi

Thermally oxidized porous silicon samples were modified using alkoxysilane aminopropyl-triethoxysilane (APTES). The silane molecule binds end ($-OCH_2CH_3$) to activate the solid surface. The $-NH_2$ end is the exposed free group to react with the molecule of interest. PSi structures were immersed in an APTES/toluene solution (5% v/v) for 90 minutes. The non-specific silane binding was eliminated by strongly rinsing the silanized surface with toluene, ethanol and ethanol/$H_2O$ (1:1). The samples were dried under the stream of $N_2$ and baked in an oven (Memmert UM200) at 110° C. during 15 minutes. Due to the high reactivity of the sulfhydryl and amine groups, the APTES-PSi modified samples were used immediately after the surface treatment. Crosslinking of MMP proteins to PSM was performed via the two-step conjugation protocol described above, based on the chemical functionalities of the aminosilane and protein. Glutaraldehyde (GTA) solution at 2.5% v/v concentration was used to activate the amine group of the aminosilane APTES towards protein binding. Eventual self-aggregation of glutaraldehyde (GTA) was reduced using freshly prepared solutions. The GTA-APTES-PSM modified samples were then rinsed with PBS buffer and dried under a stream of $N_2$. The incubation time of the silanized PSM-substrates in glutaraldehyde (GTA) solution did not exceed 20 minutes, to reduce the molecular polymerization.

Method 2: Peptide Binding

After deoxidation with diluted HCl (1/10 in deionized water), the porous silicon sample was incubated in 20 μM of the biotinylated SPGLSLVSHMQT peptide (diluted in PBST/10) for 2 hours, followed by a thorough rinsing step to remove unbound and excess peptide. Then, the sample was incubated in Bovine Serum Albumin (BSA 0.1% in PBS/10) for 1 hour. In the next step, various concentrations of matrix metalloproteinase (MMP) solutions (diluted in PBS/10) were added to PSM substrates and allowed to adsorb for one hour, followed by a rinsing step. Drying with nitrogen was performed after each surface modification step. All rinsing steps were first performed with PBS/10 and then with deionized water to avoid salt crystal formation when samples were dried with nitrogen.

The results are presented on FIGS. 10 and 11.

Silanization of the oxidized porous silicon structures, followed by glutaraldehyde (GTA) chemistry was found to give very inconsistent results in molecules' capturing. On the contrary, the use of the Si-specific SPGLSLVSHMQT peptide linked to the naked porous silicon micro-cavity substrate (PSM) was found to be a good alternative method to attach the anti-MMP-8 human antibody, previously modified with streptavidin (STV). The peptide functionalized porous silicon micro-cavity substrate (PSM) was further used to sense MMP-8 at much higher detection sensitivities compared to the silanized structures.

The results reveal the importance of the applied functionalization procedure when porous silicon micro-cavity substrates (PSM) are used for specific detection via antibodies especially at low concentrations.

The invention claimed is:

1. A p-doped silicon substrate comprising a peptide adsorbed to the surface of the substrate, wherein the peptide consists of 5 to 30 amino acid residues, said peptide comprising an amino acid sequence selected from SEQ ID NO:2, and amino acid sequences with at least 80% sequence identity with SEQ ID NO:2, wherein optionally the peptide is covalently coupled at one end to a biological ligand.

2. A p-doped silicon substrate according to claim 1, wherein the silicon substrate is a porous silicon substrate having pores diameters ranging from 15 nm to 200 nm.

3. A p-doped silicon substrate according to claim 1, wherein the biological ligand is selected from the group consisting of an antibody, a receptor protein, double stranded DNA, double stranded RNA, single stranded DNA, and single stranded RNA.

4. A process of preparing a p-doped silicon substrate as defined according to claim 1 comprising at least the step of contacting a silicon substrate with a peptide consisting of 5 to 30 amino acid residues, said peptide comprising an amino acid sequence selected from SEQ ID NO:2, and amino acid sequences with at least 80% sequence identity with SEQ ID NO:2, wherein optionally the peptide is covalently coupled at one end to a biological ligand.

5. A process according to claim 4, further comprising a covalent coupling step of a biological ligand selected from the group consisting of an antibody, a receptor protein, double stranded DNA, double stranded RNA, single stranded DNA, and single stranded RNA.

6. A microelectronic comprising the p-doped silicon substrate according to claim 1.

7. A silicon nano-particle comprising the p-doped silicon substrate according to claim 1.

8. A pharmaceutical composition comprising a silicon nano-particle comprising the p-doped silicon substrate as defined according to claim 1 as a carrier for drug delivery.

9. An optical or electrical biosensor comprising the p-doped silicon substrate as defined according to claim 1.

10. The p-doped silicon substrate of claim 1, wherein the amino acid sequence is selected from SEQ ID NO: 2 and amino acid sequences with at least 90% sequence identity with SEQ ID NO: 2.

11. The p-doped silicon substrate of claim 1, wherein the amino acid sequence is selected from SEQ ID NO: 2 and amino acid sequences with at least 95% sequence identity with SEQ ID NO: 2.

12. The p-doped silicon substrate of claim 1, wherein the peptide comprises the amino acid sequence of SEQ ID NO: 2.

13. The p-doped silicon substrate of claim 1, wherein the peptide consists of the amino acid sequence of SEQ ID NO: 2.

* * * * *

SEQUENCE LISTING

```
<160> NUMBER OF SEQ ID NOS: 12

<210> SEQ ID NO 1
<211> LENGTH: 12
<212> TYPE: PRT
<213> ORGANISM: Artificial sequence
<220> FEATURE:
<223> OTHER INFORMATION: Peptide for the functionalization of silicon
      substrate

<400> SEQUENCE: 1

Leu Leu Ala Asp Thr Thr His His Arg Pro Trp Thr
1               5                   10

<210> SEQ ID NO 2
<211> LENGTH: 12
<212> TYPE: PRT
<213> ORGANISM: Artificial sequence
<220> FEATURE:
<223> OTHER INFORMATION: Peptide for the functionalization of silicon
      substrate

<400> SEQUENCE: 2

Ser Pro Gly Leu Ser Leu Val Ser His Met Gln Thr
1               5                   10

<210> SEQ ID NO 3
<211> LENGTH: 5
<212> TYPE: PRT
<213> ORGANISM: Artificial sequence
<220> FEATURE:
<223> OTHER INFORMATION: Peptide linker

<400> SEQUENCE: 3

Gly Gly Gly Ser Lys
1               5

<210> SEQ ID NO 4
<211> LENGTH: 17
<212> TYPE: PRT
<213> ORGANISM: Artificial sequence
<220> FEATURE:
<223> OTHER INFORMATION: Peptide for the functionalization of silicon
      substrate

<400> SEQUENCE: 4

Ser Pro Gly Leu Ser Leu Val Ser His Met Gln Thr Gly Gly Gly Ser
1               5                   10                  15

Lys

<210> SEQ ID NO 5
<211> LENGTH: 12
<212> TYPE: PRT
<213> ORGANISM: Artificial sequence
<220> FEATURE:
<223> OTHER INFORMATION: Putative peptide for the functionalization of
``` silicon substrate

<400> SEQUENCE: 5

Ser Val Ser Val Gly Met Lys Pro Ser Pro Arg Pro
1               5                   10

<210> SEQ ID NO 6
<211> LENGTH: 12
<212> TYPE: PRT
<213> ORGANISM: Artificial sequence
<220> FEATURE:
<223> OTHER INFORMATION: Putative peptide for the functionalization of
      silicon substrate

<400> SEQUENCE: 6

Gly Gln Pro Leu Ile Ala His Ser Thr Lys Leu Leu
1               5                   10

<210> SEQ ID NO 7
<211> LENGTH: 12
<212> TYPE: PRT
<213> ORGANISM: Artificial sequence
<220> FEATURE:
<223> OTHER INFORMATION: Peptide for the functionalization of silicon
      substrate

<400> SEQUENCE: 7

Phe Pro Asn Pro Pro Met Thr Ile Thr Met Pro
1               5                   10

<210> SEQ ID NO 8
<211> LENGTH: 12
<212> TYPE: PRT
<213> ORGANISM: Artificial sequence
<220> FEATURE:
<223> OTHER INFORMATION: Putative peptide for the functionalization of
      silicon substrate

<400> SEQUENCE: 8

Ser Val Ser Val Gly Met Lys Pro Ser Pro Arg Pro
1               5                   10

<210> SEQ ID NO 9
<211> LENGTH: 12
<212> TYPE: PRT
<213> ORGANISM: Artificial sequence
<220> FEATURE:
<223> OTHER INFORMATION: Putative peptide for the functionalization of
      silicon substrate

<400> SEQUENCE: 9

Gly Ser Met Ser Pro Tyr Val Arg Trp Tyr Thr Pro
1               5                   10

<210> SEQ ID NO 10
<211> LENGTH: 12
<212> TYPE: PRT
<213> ORGANISM: Artificial sequence
<220> FEATURE:
<223> OTHER INFORMATION: Putative peptide for the functionalization of
      silicon substrate

<400> SEQUENCE: 10

Thr Leu Gly Phe Arg Asn Ser Asp Tyr Leu Tyr Ile
1               5                   10

<210> SEQ ID NO 11

```
<211> LENGTH: 12
<212> TYPE: PRT
<213> ORGANISM: Artificial sequence
<220> FEATURE:
<223> OTHER INFORMATION: Putative peptide for the functionalization of
      silicon substrate

<400> SEQUENCE: 11

Ser Val Ser Val Gly Met Lys Pro Ser Pro Arg Pro
1               5                   10

<210> SEQ ID NO 12
<211> LENGTH: 12
<212> TYPE: PRT
<213> ORGANISM: Artificial sequence
<220> FEATURE:
<223> OTHER INFORMATION: Putative peptide for the functionalization of
      silicon substrate

<400> SEQUENCE: 12

Ala Asn His Asn Lys Met Leu Gln Tyr Arg Gln Pro
1               5                   10
```